United States Patent [19]

Ngo et al.

[11] Patent Number: 5,219,529
[45] Date of Patent: Jun. 15, 1993

[54] CARTRIDGE ASSEMBLY

[75] Inventors: That T. Ngo; Raphael C. Wong, both of Irvine, Calif.

[73] Assignee: UniSyn Technologies, Inc., Tustin, Calif.

[21] Appl. No.: 947,905

[22] Filed: Sep. 14, 1992

Related U.S. Application Data

[63] Continuation of Ser. No. 389,703, Aug. 4, 1989, abandoned, which is a continuation-in-part of Ser. No. 70,764, Jul. 7, 1987, Pat. No. 4,892,710.

[51] Int. Cl.⁵ .................................................. B01L 3/00
[52] U.S. Cl. .................................. 422/102; 73/864.91; 206/534; 215/329; 422/102

[58] Field of Search ............................... 422/100-102; 215/329; 73/864.91; 206/534

[56] References Cited

U.S. PATENT DOCUMENTS 4,871,675 10/1989 Coupek et al. ................. 422/101 X Primary Examiner—Jill A. Johnston
Attorney, Agent, or Firm—Edward S. Irons

[57] ABSTRACT

A cartridge includes a male end, a female end and an internal chamber defined by a filter adjacent the male and female ends. The cartridge is specifically designed to be stackable with additional cartridges, as the male end of one cartridge can close the female end of a different cartridge. The cartridges are useful in holding samples for analysis.

8 Claims, 1 Drawing Sheet

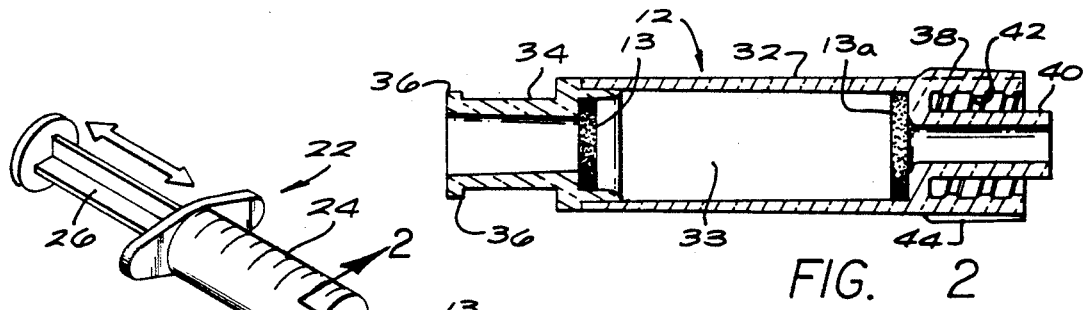
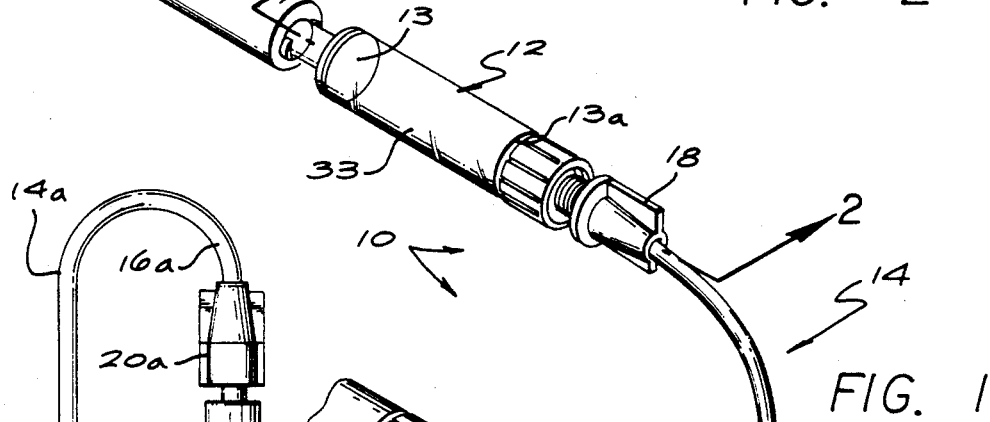
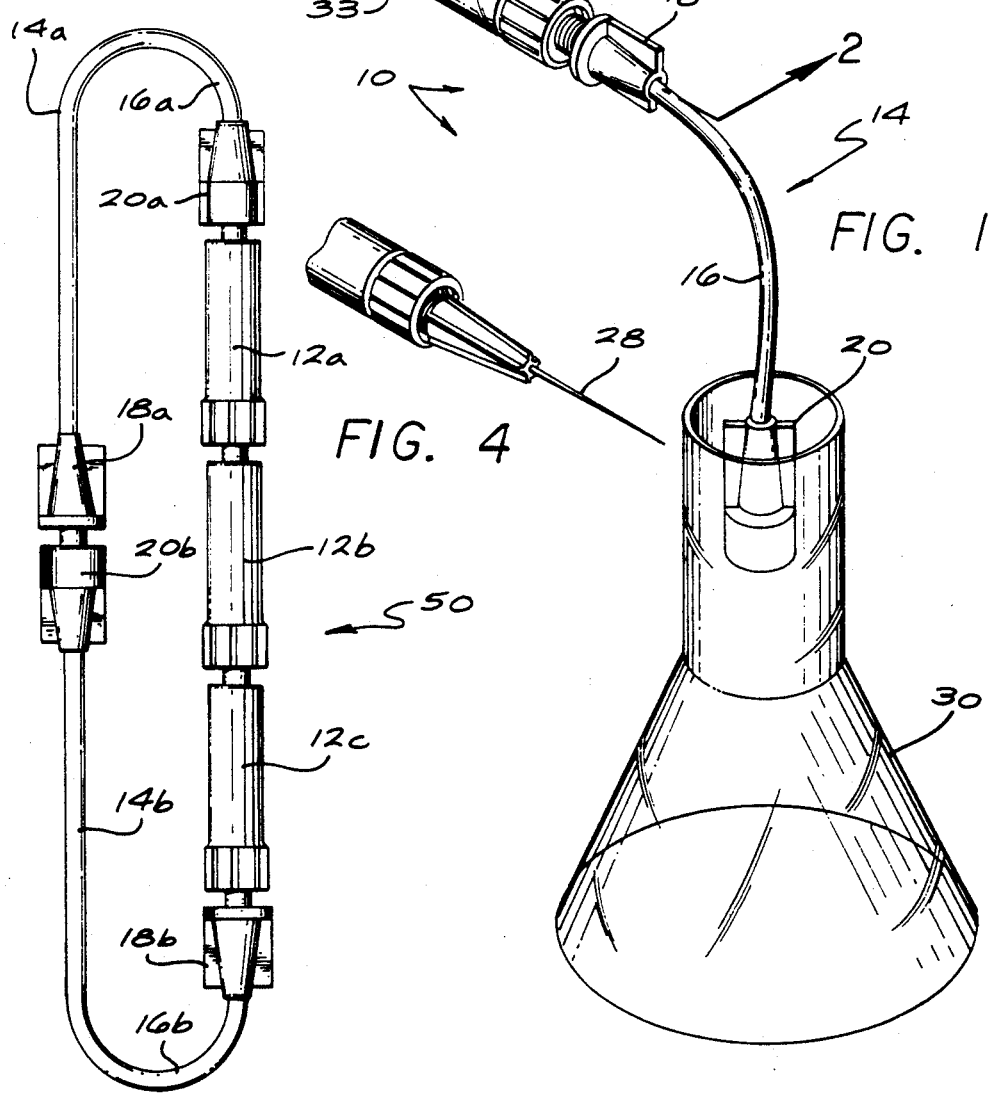

CARTRIDGE ASSEMBLY

BACKGROUND OF THE INVENTION

This is a continuation of Ser. No. 07/389,703, filed Aug. 4, 1989, now abandoned, which is a continuation-in-part of Ser. No. 07/070,764 filed Jul. 7, 1987, issued as U.S. Pat. No. 4,892,710 on Jan. 9, 1990.

This invention relates to a cartridge useful as a sampling or test device. In one of its more particular aspects, this invention relates to a cartridge containing particulate material and adapted for use in sampling and analyzing biological and chemical materials.

Devices for sampling materials to be analyzed and for analyzing various materials, particularly materials of a biological character, are well-known. Most such devices, however, are cumbersome and lack the flexibility that is desirable in sampling and analyzing various biological materials. In addition, conventional analysis frequently require passing an impure mixture containing the biological component to be detected through a suitable column to selectively adsorb the desired component from the mixture. The desired component is then later eluted from the column in a purified form for analysis or whatever other purposes the component is desired. For example, various processes are known for the purification of monoclonal antibodies utilizing an immobilized protein A adsorbent and various buffer solutions. In these processes, conventional columns are used to contain the adsorbent.

With respect to particular devices for use in various biological processes, U.S. Pat. No. 4,212,948 describes the use of centrifugation tubes containing a liquid cushioning agent.

U.S. Pat. No. 4,409,105 describes a column containing dried gamma globulin affixed to a solid carrier.

U.S Pat. No. 4,476,093 describes a kit containing a water insoluble anti-human alpha$_2$-macroglobulin antibody and a gel of allyl dextran crosslinked with N,N$^1$-methylenebisacrylamide of a gel of polyvinyl alcohol having many hydrophilic hydroxyl groups equilibrated with a pH 7.0–7.4 buffer solution and endotoxin marker solution and a buffer solution.

U.S. Pat. No. 4,543,328 describes a process and device for detecting pathogens in which a biocompatible adsorbent adsorbs the pathogen from a blood sample, with the pathogen being thereafter detected by conventional means.

U.S. Pat. No. 4,469,630 describes a chromatographic separation of monoclonal antibody type IgG from mouse ascites fluid. A particulate silica gel of specified particle size and pore size to which polyethylenimine is bound is utilized in the separation.

U.S. Pat. No. 4,490,290 describes a process for recovering immunoglobulins from natural sources such as milk or blood serum utilizing an insoluble carrier having low affinity monoclonal antibodies bound thereto.

It would be desirable to provide a convenient to use device which is portable, which can be used for sampling purposes or to purify or test for various materials, especially materials of biological interest.

Accordingly, it is an object of the present invention to provide an improved sampling and purification device.

It is another object of the present invention to provide such a device which can function both as a container for collecting or transporting samples and as a sample purification column.

Another object of the present invention is to provide such a device which can be used with varying volumes of test materials.

Another object of the present invention is to provide such a device, the use of which is characterized by speed and convenience.

It is a further object of this invention to provide such a device which can be used in conjunction with a wide variety of different particulate materials, such as adsorbents and filtration agents.

It is yet another object of the invention to provide such a device which is of a relatively simple construction and permits secure, facile attachment of other devices thereto.

Other objects and advantages of the invention will become apparent from the following detailed disclosure.

SUMMARY OF THE INVENTION

The present invention provides a cartridge comprising a male end, a female end and an internal chamber defined by filter means adjacent the male and female ends. Such cartridge is particularly suited for use in a cartridge assembly as disclosed in application Ser. No. 07/070,764 filed Jul. 7, 1987, now U.S. Pat. No. 4,892,710 wherein a closure tubing is fitted with a male end adapted to close one end of the cartridge and a female end adapted to close the other end of the cartridge. Luer locks may be utilized as closure means to insure watertight closure of the cartridge, either by means of the aforementioned closure tubing or with simple cap means.

BRIEF DESCRIPTION OF THE DRAWINGS

FIG. 1 is a perspective view showing the cartridge of the present invention in a cartridge assembly including a syringe and closure tubing in accordance with Ser. No. 07/070,764 filed Jul. 7, 1987 now U.S. Pat. No. 4,892,710.

FIG. 2 is a cross-sectional view of the cartridge of the present invention.

FIG. 3 is a side elevation of three cartridges in tandem.

FIG. 4 is a partial perspective view of a cartridge of the present invention fitted with a syringe needle.

DESCRIPTION OF THE PREFERRED EMBODIMENTS

Referring to FIG. 1 of the drawings, the numeral 10 represents a cartridge assembly including a cartridge according to the present invention. Cartridge assembly 10 consists of cartridge 12 and closure 14. Cartridge 12 will be described more particularly with regard to FIG. 2. Closure 14 consists of closure tubing 16 having a male closure 18 at one end thereof and a female closure 20 at the other end. Also shown attached to the cartridge according to the present invention in FIG. 1 is a syringe 22 which consists of a body 24 and a plunger 26.

FIG. 2 shows the cartridge 12 in greater detail. Throughout the description of the drawings, the same or similar numerals will be used to describe similar parts. As shown in FIG. 2, cartridge 12, which may, for example have a volume of 0.5 ml, 1 ml or 5 ml, comprises a body 32 including an internal cavity 33 defined by filter means 13, 13a adjacent male end 34 and female end 38, respectively. In the illustrated embodiment, male end 34 is fitted with lugs 36 and female end 38 is in the form of an inner tube 40, threads 42 and ribs 44. When lugs 36 are mated with threads 42 of some form of closure means or another cartridge, as will be described below, there is formed a luer lock which insures a watertight closure.

FIG. 3 shows a multiplicity of cartridges used in tandem. The purpose of such arrangement is to increase the volume which can be sampled in the cartridges or to increase the length of a column used for purifying a particular substance. Extended column 50 consists of 3 cartridges 12a, 12b and 12c connected in tandem, the lugs 36 of the male end of one cartridge being threadedly engaged with the threads 42 of the female end of another cartridge, forming a luer lock. As shown in FIG. 3, cartridge 12a is thus connected to cartridge 12b which in turn is connected to cartridge 12c. The male end of cartridge 12a is closed in the illustrated embodiment by means of the female closure 20a while the female end of cartridge 12c is closed by means of male closure 18b. Since in the illustrated embodiment a single closure 14 is of insufficient length to close the tandem assembly of cartridges 12a, 12b and 12c, two closures 14a and 14b connected by means of male closure 18a of closure 14a and female closure 20b of closure 14b are employed. The combined length of closure tubings 16a and 16b is adequate to conveniently close the tandem assembly of cartridges 12a, 12b and 12c as depicted. Alternatively, simple closure means (such as screw caps) at the male end of cartridge 12a and the female end of cartridge 12c, or a single closure having a longer tubing, could be used.

Filter means 13, 13a serve as retaining means for 33 defined in the interior of the cartridge 12 by filter means 13, 13a and the exterior wall is advantageously at least partially filled with particulate material to be used for treatment of a liquid which will subsequently be introduced into chamber 33. Thus, one important characteristic of filter means 13, 13a is that it should be at least substantially impermeable to the particulate material which is to be retained thereby. As in many instances contamination of purified or otherwise treated liquids by the particulate material is not acceptable, in preferred embodiments the filter means is essentially completely impermeable to the particulate material in chamber 33.

In addition, filter means 13, 13a must be of sufficient porosity to permit introduction of a liquid to be treated into chamber 33, as well as to allow for rinsing or other standard operations employing liquid reagents to be carried out on the contents of chamber 33 without undue difficulty. Accordingly, it is also necessary that filter means 13, 13a remain permeable to flow of liquids therethrough.

A wide variety of materials are already known which are permeable to the flow of liquids yet of sufficiently small pore size so as to retain particulate material within chamber 33. In principle, any porous material which is inert to the particular reagents employed in a given system may be used, provided that the pore size of the material is sufficiently low so as to retain substantially all of the particles of the particulate matter within chamber 33 (i.e., a pore size less than the diameter of most of the particles). For use with materials for treatment of typical biological fluids in cartridges according to the present invention, suitable filters may be prepared from a wide variety of materials such as polyethylene, polypropylene, polyvinylidene fluoride, polystyrene, polytetrafluoroethylene, styrene-acrylonitrile, ethylene-vinyl acetate and sintered glass. When used in the preparation of filters in accordance with the invention, these and other materials will typically be selected to have a porosity on the order of from about 5 to about 500 microns, preferably about 20 to about 35 microns. One particularly suitable material is high density polyethylene with a porosity of about 25 microns; one such material is commercially available from Porex Technologies, Fairburn, Ga. under the designation POREX$^R$. The filter means 13, 13a may also vary in thickness over a fairly wide range, a primary consideration being that the particulate material should be retained within the cartridge in the absence of any substantial barrier to the necessary flow of liquid. For a material such as high density polyethylene, having a porosity of about 25 microns, a thickness on the order of about 0.5 mm to about 6 mm, preferably about 1 mm to about 3 mm, is suitable in a typical cartridge of 40 mm length and 5 ml volume. Depending on factors such as the size of the cartridge, the composition and dimensions of the filter and the specific combinations of particulate material and liquids employed, significant variations from the above would be possible without departing from the spirit and scope of the invention; all such modifications would of course be well within the realm of routine experimentation and testing.

In sampling, a single cartridge 12 is filled with the material to be sampled, for example, by means of a syringe as shown in FIG. 1. After disconnecting the syringe from the cartridge, the sample is maintained secure and uncontaminated by suitable closure means. For most purposes, each end of the cartridge may be closed by individual closure means, such as screw caps accommodating the respective male and female ends or like devices. Alternatively, closure 14 may be employed with the female closure 20 securely closing male end 34 of cartridge 12 by means of lugs 36 and threads within female closure 20 (not shown) and female end 38 of cartridge 12 similarly closed by male closure 18 as shown in FIG. 1, the threads 42 inside female end 38 of cartridge 12 engaging the external threads of male closure 18 as shown in FIG. 1. In either case both ends of cartridge 12 may thus be securely closed by luer locks.

For purification of a particular material, a cartridge 12 is filled with a suitable particulate material. Suitable particulate materials include ion-exchange gels, molecular sieve gels, chelating resins, activated carbon particles, hydrophobic gels and affinity gels. In particular, a solid adsorbent such as an immobilized Protein A or Protein G is especially advantageous for such uses.

Many such suitable particulate adsorbents are commercially available. A purified Protein A coupled to cross-linked agarose beads by chemically stable amide bonds can be obtained from Bio-Rad Laboratories, Richmond, California as Affi-Gel ® Protein A. Protein A-Agarose is also available from Zymed Laboratories, Burlingame, Calif. This product is described as a pure Protein A coupled to CNBr-activated Sepharose ® 4B. A similar product, Protein A Sepharose ® CL-4B is also available from Pharmacia Fine Chemicals, Uppsala, Sweden. Protein A-Ultrogel ® is available from Reactifs IBF, France. It is described as a biospecific affinity chromatography adsorbent able to interact with different immunoglobulins G from different mammals and is prepared by immobilizing electrophoretically pure Protein A to a glutaraldehyde-activated gel. Protein A covalently coupled to cross-linked beaded agarose is also available from Pierce Chemical Co.

An immobilized Protein A or Protein G can also be provided using the techniques disclosed in U.S. Pat. No. 4,582,875, assigned to the same assignee as the present invention, the disclosure of which is hereby incorporated by reference. This patent generally teaches the activation of hydroxyl group-containing polymeric carriers using 2-fluoro-1-methylpyridinium toluene-4-sulfonate (FMP). Such activated polymers are commercially available from BioProbe International, Inc., Tustin, Calif. Avid-Gel TM FMP-activated hydrophilic gel is an FMP-activated polymer of N-acryloyl-2-amino-2-hydroxymethyl-1, 3-propanediol (Trisacryl GF 2000, Reactifs, IBF, France). Avid-Gel F TM FMP-activated hydrophilic gel is an FMP-activated hydrophilic polyvinyl alcohol composed exclusively of C, H and O atoms (Fractogel TSK, E. Merck, Darmstadt, Germany). Both can be used to provide an immobilized Protein A.

It will of course be understood that materials other than the described adsorbents may also be used in cartridges according to the present invention, and that such cartridges may be used in methods other than the treatment of biological fluids. Any solid material that would have utility in chromatographic treatment of a liquid composition in a conventional chromatography column might for example be profitably employed in the form of a cartridge in accordance with the present invention, to the extent that it is desired to provide such material in a premeasured amount and/or in a container which permits flow of the liquid composition through the solid material. Thus, a combination of cartridge 12 with a needle 28 and syringe 22 provides a particularly advantageous means for obtaining a liquid sample of a specified volume admixed with a solid material, in a container which may readily be closed for storage or transport of the liquid using simple mechanical means.

One particularly preferred embodiment of a cartridge in accordance with the invention provides a predetermined amount of a particulate material, for example a suitable adsorbent, in a single cartridge which is sealed at both ends by simple mechanical closure means, such as screw caps. By combination of the male end of one cartridge with the female end of a second cartridge, it is further possible to provide in effect a column of a desired length simply by adding the requisite number of cartridges; moreover, the material in each cartridge may be the same or different, thereby permitting the user to devise a selected sequential treatment method by arranging cartridges containing appropriate materials in the proper order through the simple expedient of a mechanical interconnection. As each such cartridge may be provided in a form ready for use after removal of end closure means, the invention provides a dramatic improvement in the ease with which a wide variety of procedures, such as chromatography or purification of biological fluids, may be effected.

Alternatively, as shown in FIG. 1, the cartridge of the present invention may be provided with a closure 14 so as to form a cartridge assembly in accordance with the teachings of co-pending application Ser. No. 07/070,764 filed Jul. 7, 1987. As previously indicated, in such an arrangement female closure 20 securely closes male end 34 of the cartridge 12 and male closure 18 closes female end 38. In use, the female closure 20 is uncapped from the male end 34 of cartridge 12 and placed in a container such as flask 30. Closure 14 including male closure 18, closure tubing 16 and female closure 20 thus serves as a conduit for conducting liquid from the cartridge 12 into flask 30. After buffering the adsorbent contained within cartridge 12 and washing by means of a syringe, as shown in FIG. 1, the sample to be purified is then passed through cartridge 12 and then unadsorbed material passes through closure 14 into flask 30. After rinsing the column comprised of cartridge 12 and the adsorbent contained within the cartridge with a suitable buffer, the eluate in flask 30 is discarded and the female closure 20 is placed into a collection container which may be similar to flask 30. Using the syringe as before, suitable buffer is passed through the cartridge to elute the desired material from the adsorbent and the eluate is collected in the collection container. The eluate is the purified component which is eluted from the adsorbent in cartridge 12. Conversely, the sample can be purified by passing it through the cartridge to remove unwanted contaminants by adsorption of the contaminants to the adsorbent. The desired materials are not adsorbed and thus passed through closure 14 into flask 30. For example, in a column containing immobilized protein A, if a mixture of the Fab and Fc antibody chains is applied to the column, the Fc chain is adsorbed upon the column while the Fab chain passes through the column and can be recovered in the flask.

Thus it can be seen that a cartridge comprising male and female ends and an internal cavity defined by filter means serves as a convenient, practical means for providing measured quantities of adsorbent or other particulate material for use in treatment of liquids, as well as a relatively inexpensive, self-contained chamber for carrying out such treatments. Use of the cartridge of the present invention facilitates and simplifies manipulations and speeds up the purification process. For instance, using a syringe luer locked to the cartridge of the present invention decreases process time from several hours to about thirty minutes or less.

The foregoing description of the invention has been directed to particular preferred embodiments for purposes of explanation and illustration. It will be apparent, however, to those skilled in the art that many modifications and changes in particular methods and materials may be made without departure from the scope and spirit of the invention. For example, a number of cartridges greater or lesser than the numbers shown in the drawings can be utilized to provide columns of varying lengths. Also, the cartridge may be longer or shorter in length, narrower or wider in diameter to suit particular uses. Further, as pointed out above, one or more cartridges may be used to form columns which are closed by simple closure means or by using, for example, closure tubing of various lengths pursuant to application Ser. No. 07/070,764 now U.S. Pat. No. 4,892,710. In addition, other processes than those specifically mentioned herein may be conducted utilizing the cartridge of the present invention. It is applicant's intention in the following claims to cover all such equivalents, modifications and changes that fall within the true spirit and scope of the invention.

What is claimed is:

1. A cartridge comprising a chamber, said chamber being defined by a male end and a female end, said male and female ends being spaced apart by an integral wall,
   each of said male and said female ends being provided with an opening into said chamber,
   said male end terminating in a lug means, said female end comprising reciprocating thread means on an inside wall of said opening of said female end for engagement of said lug means of said male end, and filter means positioned adjacent said opening of each of said male means and said female means into said chamber, whereby a male end of a first cartridge may be secured by said lug means to reciprocating thread means of a female end of a second cartridge.

2. A cartridge as defined in claim 1 in which said chamber contains particulate material.

3. A cartridge as defined in claim 2, wherein said particulate material is an adsorbent.

4. A cartridge as defined by claim 3 wherein said adsorbent is selected from the group consisting of ion-exchange gels, molecular sieve gels, chelating resins, activated carbon particles, hydrophobic gels, affinity gels, immobilized protein A and immobilized protein G.

5. A cartridge as defined by claim 1 wherein said filter means has a thickness in the range of 0.5 mm to about 6 mm.

6. A cartridge as defined by claim 5 wherein said thickness of said filter is in the range of about 1 mm to about 3 mm.

7. A cartridge as defined in claim 1 wherein said filter means comprises a high density polyethylene having a porosity in the range of about 5 to about 500 microns and a thickness in the range of about 0.5 mm to about 6 mm.

8. A cartridge as defined in claim 7 wherein said porosity is in the range of about 20 to about 35 microns and the thickness is in the range of about 1 mm to about 3 mm.

* * * * *